US00PP33571P2

(12) United States Plant Patent
Van Swieten

(10) Patent No.: US PP33,571 P2
(45) Date of Patent: Oct. 19, 2021

(54) ***PHALAENOPSIS* ORCHID PLANT NAMED 'PHALHOQGAI'**

(50) Latin Name: ***Phalaenopsis* hybrid**
Varietal Denomination: PHALHOQGAI

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/998,111

(22) Filed: Aug. 20, 2020

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Jul. 10, 2021 p. 1.*

* cited by examiner

*Primary Examiner* — Annette H Para
(74) *Attorney, Agent, or Firm* — Jondle & Associates, P.C.

(57) ABSTRACT

A new and distinct variety of *Phalaenopsis* plant named 'PHALHOQGAI', particularly characterized by white flowers with greenish-yellow-white lips, concave flower shape, compact plant, and is propagated by meristem tissue culture, is disclosed.

3 Drawing Sheets

Genus and species: *Phalaenopsis* hybrid.
Variety denomination: 'PHALHOQGAI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHOQGAI'.

The new *Phalaenopsis* plant is a product of a planned breeding program conducted by the inventor in Bleiswijk, the Netherlands. The objective of this breeding program was to create a new, compact *Phalaenopsis* plant with white flowers and greenish-yellow-white lips, suitable for potted plant production.

The new *Phalaenopsis* plant 'PHALHOQGAI' is a result of cross-pollination made by the inventor in April 2011 in Bleiswijk, the Netherlands, of the proprietary female, or seed parent, *Phalaenopsis* hybrid '01-3469' (unpatented) with the proprietary male, or pollen parent, *Phalaenopsis* hybrid '21232-01' (unpatented).

The new *Phalaenopsis* was selected by the inventor as a single plant within the progeny of the stated cross-pollination in a controlled greenhouse in Bleiswijk, the Netherlands, in June 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 16, 2019 (Application no. 2019/0996), by Applicant who obtained the subject matter disclosed directly from the inventor. 'PHALHOQGAI' has not been made publicly available or sold anywhere in the world prior to the effective filing date of this application with the exception of sales or disclosures made one year or less before the effective filing date of this claimed invention by Applicant who obtained 'PHALHOQGAI' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHOQGAI' as a new and distinct variety of *Phalaenopsis* plant:

1) Plant has white flowers with greenish-yellow-white lips;
2) Flower shape is concave; and
3) Plant is compact.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in July 2020. Colors in the photographs may differ from the color values cited in the detailed botanical description, which accurately describe the actual colors of the new variety.

DESCRIPTION OF THE NEW VARIETY

Figure 1:
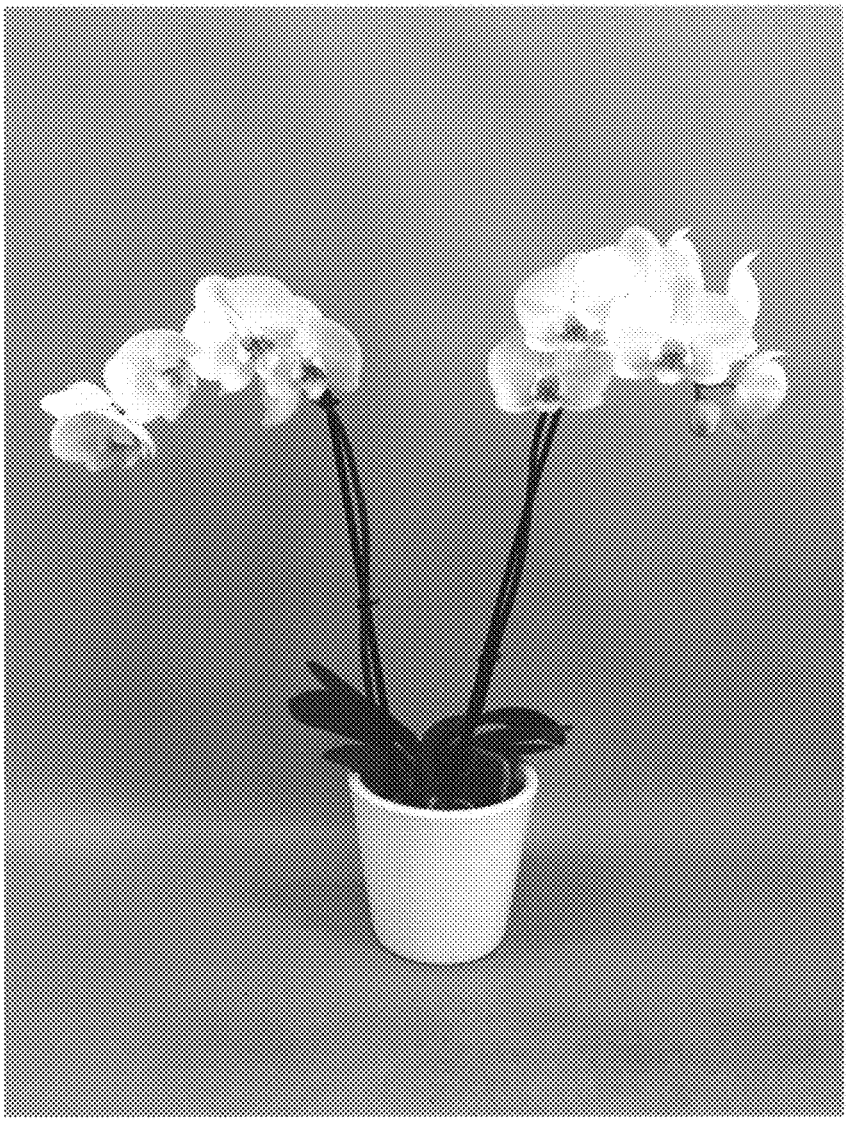
FIG. 1 shows the overall plant habit, including blooms, buds, and foliage of 'PHALHOQGAI'.
Figure 2:
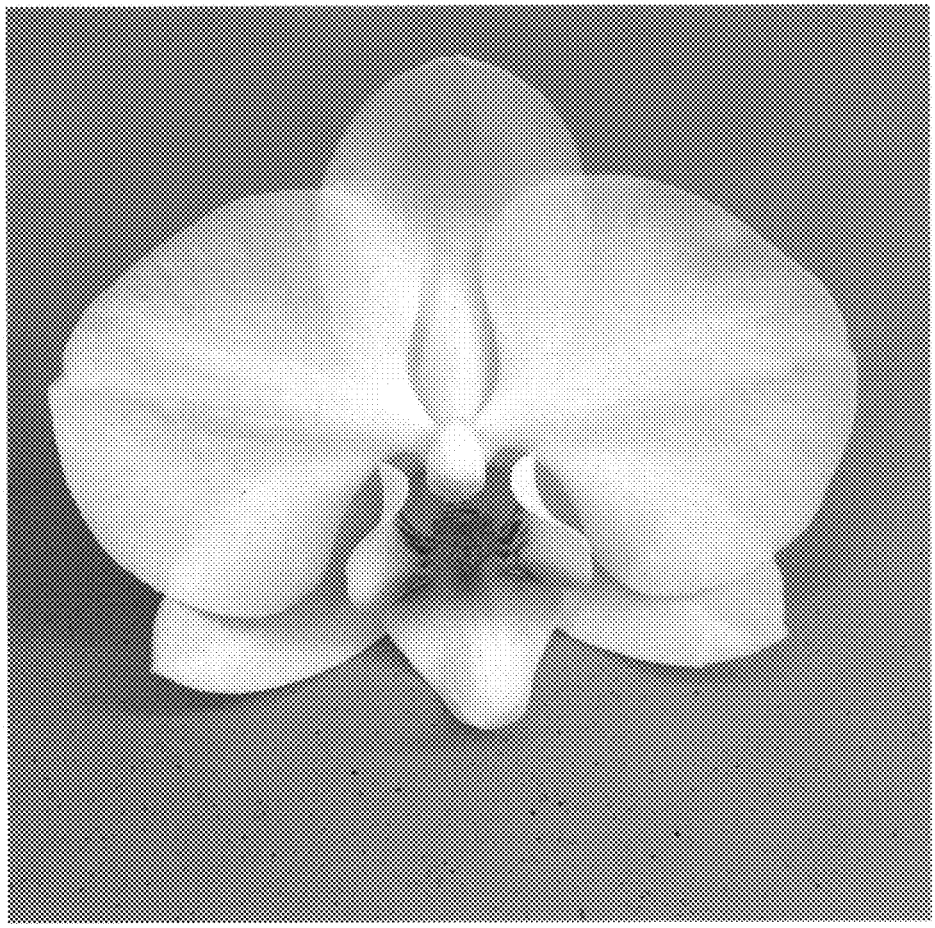
FIG. 2 shows a close-up of a flower of 'PHALHOQGAI'.
Figure 3:
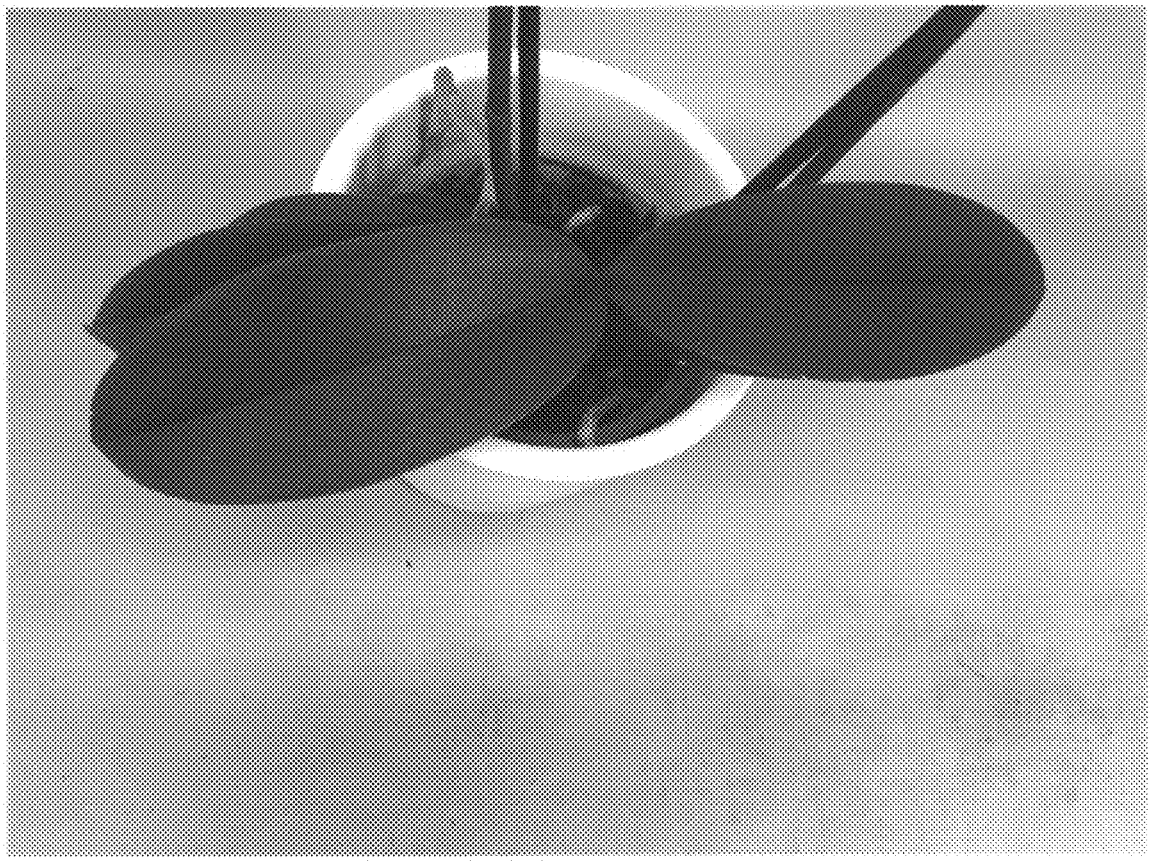
FIG. 3 shows an overhead view of the leaves of 'PHALHOQGAI'.

The following detailed description sets forth the distinctive characteristics of 'PHALHOQGAI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in July 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHOQGAI'.

Parentage:

*Female parent*.—*Phalaenopsis* cultivar '01-3469' (unpatented).

*Male parent*.—*Phalaenopsis* cultivar '21232-01' (unpatented).

Propagation:

*Type*.—Meristem tissue culture.

Roots:

*Root description*.—Greyed-green (something between RHS 190B and 190C) colored roots with branching lateral roots having light yellow-green (RHS 145B) with a hint of purplish-red (RHS N77B) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 50.0 cm to 55.0 cm.

*Width* (*measured from leaf tips*).—About 25.0 cm to 27.0 cm.

*Vigor*.—Strong.

Leaves:

*Mature leaves*.—Quantity per plant: 7 to 8 leaves are produced before flowering. Length (fully expanded): 13.0 cm to 16.0 cm. Width: 5.5 cm to 6.5 cm. Position of the broadest part of the leaf: At the middle. Shape: Oblong. Base shape: Moderately elongated. Apex: Unequal obtuse. Leaf blade angle with the petiole (measured from the horizontal position): Between 15 degrees and 35 degrees. Leaf margin: Entire. Color: Upper surface: RHS 146A. Lower surface: RHS 146B. Texture (both upper and lower surfaces): Smooth. Thickness: 2.5 mm to 2.8 mm. Variegation: Absent. Venation: Pattern: Parallel. Color of the midvein: Upper surface: RHS 147A. Lower surface: RHS 146A.

Peduncle:

*Quantity per plant*.—1 to 2.

*Number of flowers per peduncle*.—9 to 12.

*Length*.—50.0 cm to 55.0 cm.

*Diameter*.—5.2 mm to 5.5 mm.

*Strength*.—Strong.

*Aspect*.—Upright to slightly pendent.

*Texture*.—Smooth.

*Color*.—Yellow-green (RHS 146C) with a touch of brown (RHS 200B) at the base and slightly lighter brown (RHS 200C) toward inflorescence.

*Internode length*.—1.0 cm to 3.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 220.0 mm to 270.0 mm.

*Flowering time*.—First flowers can be expected 10 to 11 months after planting in a 12-cm pot.

*Flower*.—Height: 70.0 mm to 75.0 mm. Diameter: 90.0 mm to 95.0 mm. Depth of lip: 25.0 mm to 27.0 mm.

*Flower longevity*.—On the plant: 8 to 11 weeks.

*Flower shape*.—Concave.

*Fragrance*.—Absent.

*Flower bud*.—Average size: Large. Length: 23.0 mm to 25.0 mm. Width: 19.0 mm to 21.0 mm. Shape: Egg shaped. Color: Yellow-green (something in between RHS 145C and N144D) with a touch of very light purple (RHS 76B).

*Petals*.—Arrangement: Open/free. Shape: Semi-circular. Apex: Emarginated asymmetric. Margin: Weakly undulated. Length (from base to tip): 41.0 mm to 43.0 mm. Width: 52.0 mm to 54.0 mm. Position of the broadest part of the petal: Toward the base. Color (when fully opened): Upper surface: Basic color: White (RHS NN155C). Over color: Absent. Lower surface: Basic color: White (RHS NN155C). Over color: Absent. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 45.0 mm to 47.0 mm. Width: 30.0 mm to 32.0 mm. Position of the broadest part of the dorsal sepals: At the middle. Color (when fully opened): Upper surface: Basic color: White (RHS NN155C). Over color: Absent. Lower surface: Basic color: White (RHS NN155C). Over color: Light yellow-green (RHS 145D) with a hint of light purple (RHS 76B). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals*.—Shape: Ovate. Apex: Obtuse symmetric. Margin: Entire. Length (from base to tip): 45.0 mm to 47.0 mm. Width: 28.0 mm to 30.0 mm. Position of the broadest part of the lateral sepals: At the base. Color (when fully opened): Upper surface: Basic color: White (RHS NN155C). Over color: Hint of light yellow-green (RHS 145D) at the base. Lower surface: Basic color: White (RHS NN155C). Over color: Light yellow-green (RHS 145C). Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 11.0 mm to 13.0 mm. Color of whiskers: White (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 21.0 mm to 23.0 mm. Width: 17.0 mm to 19.0 mm. Color: Upper surface: Greenish-yellow at the base on one side (at the base toward the callus RHS 5A and toward the tip RHS 151C); hint of dark pink (RHS 182D) at the base; white (RHS NN155C) toward the other side. Lower surface: Greenish-yellow on one side (at the base toward the callus RHS 5A and toward the tip RHS 151C); white (RHS NN155C) toward the other side. Number of spots and stripes on the lateral lobe (upper surface): Few stripes at the base. Color of spots and stripes on the lateral lobe (upper side): Brown (RHS 172A). Density of netting of the lateral lobe (upper surface): None. Color of the netting (upper surface): Not applicable.

*Apical lobe*.—Shape: Triangular. Margin: Entire. Length: 23.0 mm to 25.0 mm. Width: 23.0 mm to 25.0 mm. Color: Upper surface: Orange margin (RHS 172B) at the base; greenish-yellow (RHS 151C) at the base; white (RHS NN155C) toward whiskers. Lower surface: Orange margin (RHS 172B) at the base; greenish-yellow (RHS 151D) at the base; white (RHS NN155C) toward whiskers. Number of spots and stripes on the apical lobe (upper surface): None. Color of spots and stripes on the apical lobe (upper surface): Not applicable. Density of netting of the apical lobe (upper surface): None. Color of the netting (upper surface): Not applicable.

*Callus*.—Average size: Medium to large. Height: 7.0 mm to 8.0 mm. Length: 6.0 mm to 7.0 mm. Width: 5.0 mm to 6.0 mm. Color: Front and back of the callus yellow (RHS 7B); at the top (RHS 17B); dotted (RHS 170A).

Reproductive organs:

*Column*.—Length: 8.0 mm to 10.0 mm. Diameter: 5.0 mm to 6.0 mm. Color: White (RHS NN155C).

*Pollinia*.—Quantity: 2. Diameter: 1.0 mm to 1.2 mm. Color: Orange (RHS 24A).

*Ovary*.—Length: 9.0 mm to 11.0 mm. Diameter: 2.3 mm to 2.6 mm.

*Pedicel*.—Length: 36.0 mm to 38.0 mm. Diameter: 2.8 mm to 3.2 mm. Texture: Smooth. Color: Reddish-brown (RHS 200B) at the base; light yellow-green (RHS 145C to 145D) with a hint of very light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHOQGAI' differs from female parent plant '01-3469' (unpatented) in that 'PHALHOQGAI' has emarginated dorsal sepal apexes and medium curvature of the lateral lobes, whereas '01-3469' has obtuse dorsal sepal apexes and strong curvature of the lateral lobes.

'PHALHOQGAI' differs from male parent plant '21232-01' (unpatented) in that 'PHALHOQGAI' has calluses with a dotted pattern, whereas '21232-01' has calluses with a striped pattern.

'PHALHOQGAI' is most similar to the commercial *Phalaenopsis* plants named 'PHALFOWIC' (U.S. Plant Pat. No. 29,245) and 'PHALFUBNE' (U.S. Plant Pat. No. 30,395). 'PHALHOQGAI' differs from the commercial variety 'PHALFOWIC' in that 'PHALHOQGAI' has white whiskers and medium curvature of the lateral lobes, whereas 'PHALFOWIC' has greenish-yellow whiskers and strong curvature of the lateral lobes. Additionally, 'PHALHOQGAI' has shorter whiskers and shorter leaves than 'PHALFOWIC'.

'PHALHOQGAI' differs from the commercial variety 'PHALFUBNE' in that 'PHALHOQGAI' has whiskers that are white, whereas 'PHALFUBNE' has whiskers that are white at the base and yellow toward the tip. Additionally, 'PHALHOQGAI' has shorter whiskers, shorter leaves, and shorter internodes than 'PHALFUBNE'.

I claim:

1. A new and distinct variety of *Phalaenopsis* plant named 'PHALHOQGAI', substantially as described and illustrated herein.

* * * * *